United States Patent
Zhu et al.

(10) Patent No.: US 6,399,215 B1
(45) Date of Patent: Jun. 4, 2002

(54) ULTRAFINE-GRAINED TITANIUM FOR MEDICAL IMPLANTS

(75) Inventors: Yuntian T. Zhu, Los Alamos; Terry C. Lowe, Santa Fe, both of NM (US); Ruslan Z. Valiev, Ufa (RU); Vladimir V. Stolyarov, Ufa (RU); Vladimir V. Latysh, Ufa (RU); Georgy J. Raab, Ufa (RU)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/536,592

(22) Filed: Mar. 28, 2000

(51) Int. Cl.$^7$ .............................. C22C 14/00; C22F 1/18
(52) U.S. Cl. ...................... 428/544; 72/253.1; 72/272; 148/670; 148/671; 148/407; 148/421; 420/417; 428/472; 623/901; 623/924; 623/926
(58) Field of Search ................................. 428/544, 378, 428/389, 472; 623/16–23, 901, 924, 926; 420/417; 148/670, 671, 407, 421; 72/253.1, 272

(56) References Cited

U.S. PATENT DOCUMENTS

| | | | |
|---|---|---|---|
| 4,854,496 A | 8/1989 | Bugle ........................... 228/193 |
| 5,400,633 A | 3/1995 | Segal et al. .................... 72/272 |
| 5,513,512 A | 5/1996 | Segal ........................ 72/253.1 |
| 5,590,389 A | 12/1996 | Dunlop et al. ................. 419/67 |
| 5,600,989 A | 2/1997 | Segal et al. ................. 72/253.1 |
| 5,725,573 A | 3/1998 | Dearnaley et al. .............. 623/2 |
| 5,763,092 A | 6/1998 | Lee et al. .................... 428/469 |
| 5,780,755 A | 7/1998 | Dunlop et al. ................. 75/249 |
| 5,782,910 A | 7/1998 | Davidson ....................... 623/3 |
| 5,809,393 A | 9/1998 | Dunlop et al. ................. 419/61 |
| 5,817,326 A | 10/1998 | Nastasi ....................... 424/426 |
| 5,850,755 A | 12/1998 | Segal ........................... 72/261 |
| 5,904,062 A | 5/1999 | Semiatin et al. ........... 72/253.1 |

OTHER PUBLICATIONS

K. Wang, "The Use and Properties of Titanium and Titanium Alloys for Medical Applications in the USA," Mater. Sci. Eng., A213 (1996) 134–137 (no month data available).

A. Ungersbock, S. M. Perren, and O. Pohler, "Comparison of Tissue Reaction to Implants of a Beat Titanium Alloy and Pure Titanium Experimental Study on Rabbits," J. Mater. Sci.: Materials in Medicine, 5 (1994) 788–792 (no month data available).

V. Segal, V. I. Reznikov, A. E. Drobyshevskiy, and V. I. Kopylov, "Plastic Working of Metals by Simple Shear," Russian Metallurgy (1981) 1, 99–105 (no month data available).

V. V. Stolyarov, Y. T. Zhu, T. C. Lowe, R. K. Islamgaliev, and R. Z. Valiev, "A Two Step SPD Processing of the Ultrafine–Grained Titanium," NanoStructured Materials, 11, 7, 947–954 (1999) (no month data available).

S. L. Semiatin, V. M. Segal, R. E. Goforth, N. D. Frey, and D. P. DeLo, "Workability of Commercial–Purity Titanium and 4340 Steel During Equal Channel Angular Extrusion at Cold–Working Temperatures," Metallurgical and Materials Transactions A, 30A (May 1999), 1425–1435.

Primary Examiner—Robert R. Koehler
(74) Attorney, Agent, or Firm—Samuel L. Borkowsky

(57) ABSTRACT

We disclose ultrafine-grained titanium. A coarse-grained titanium billet is subjected to multiple extrusions through a preheated equal channel angular extrusion (ECAE) die, with billet rotation between subsequent extrusions. The resulting billet is cold processed by cold rolling and/or cold extrusion, with optional annealing. The resulting ultrafine-grained titanium has greatly improved mechanical properties and is used to make medical implants.

50 Claims, 1 Drawing Sheet

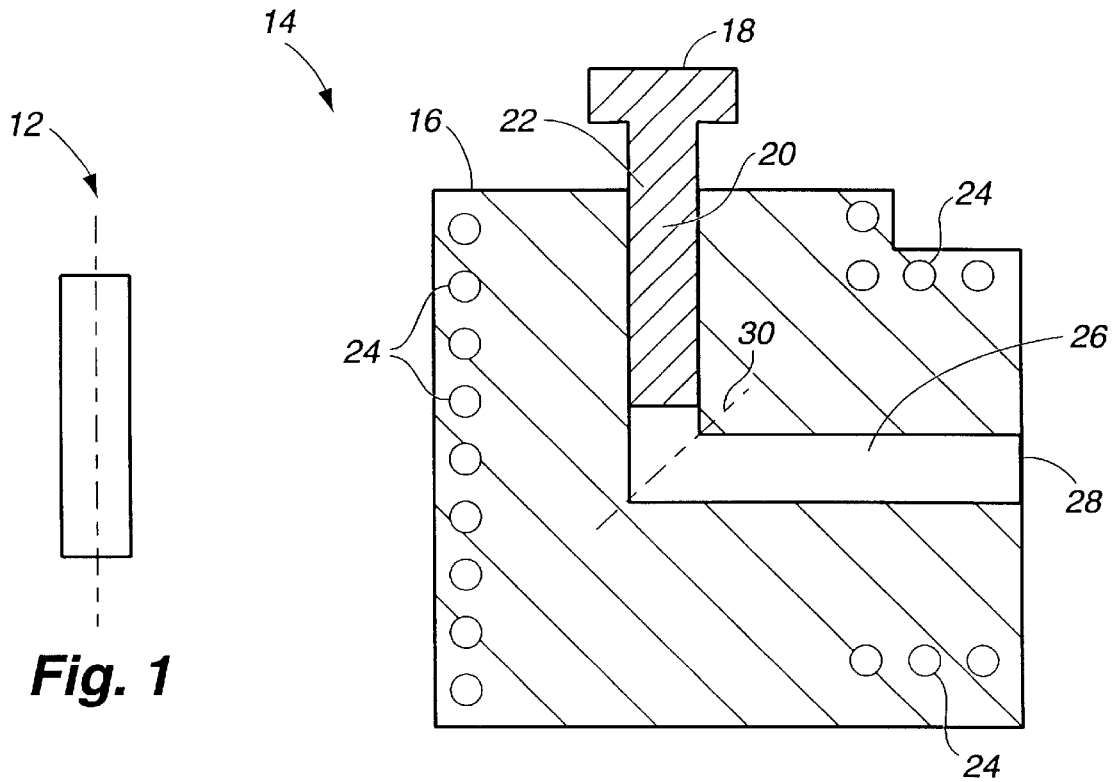
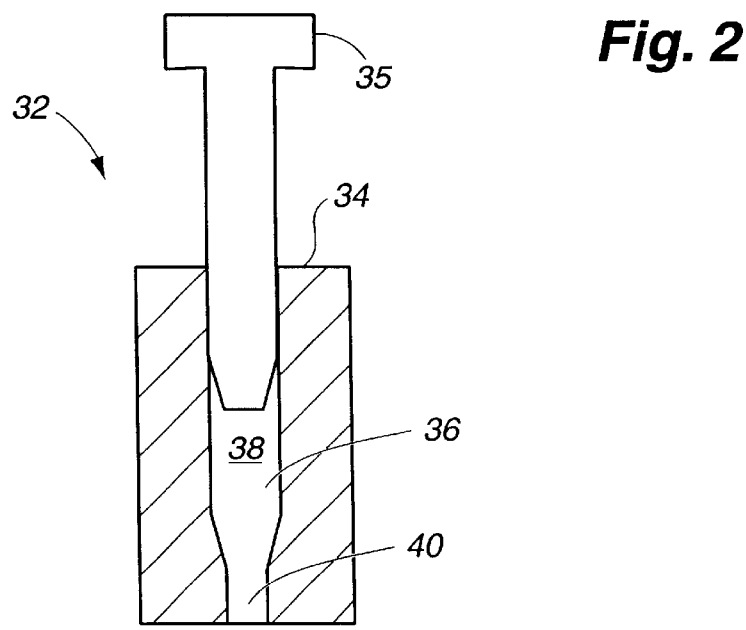

ULTRAFINE-GRAINED TITANIUM FOR MEDICAL IMPLANTS

FIELD OF THE INVENTION

The present invention relates generally to ultrafine-grained titanium and, more particularly, to medical implants and other devices made with ultrafine-grained titanium. This invention was made with government support under Contract No. W-7405-ENG-36 awarded by the U.S. Department of Energy to The Regents to the University of California. The U. S. Government has certain rights in the invention.

BACKGROUND OF THE INVENTION

Medical implants and prostheses provide structural and mechanical aid or replacement for parts of the body that can no longer provide their intended function. Implants subject to stress must bear the required loads without failure, and must also be corrosion resistant and chemically compatible with body organs and fluids since they can remain in the body for years. Implants generally include metal wires, rods, plates, screws, tubes, and other devices. Some are attached to bone to allow others to reinforce damaged bone in the body. Since they are generally much stiffer than bone, they can promote stress shielding in the attached bone that can lead to implant loosening and osteoporosis. Implants generally have a lifetime of about 7–10 years. Surgical implant replacement is possible, however usually not more than twice for a particular implant device due to bone damage created by the first implant. As a result, recommended medical procedures involving implants are generally for older people.

Titanium alloys are usually materials of choice for making medical implants. In particular, Ti-6V-4Al, a titanium alloy initially developed for aerospace applications, is currently the alloy used to make most orthopedic implants and has been described in various papers and patents. For example, U.S. Pat. No. 4,854,496 by C. M. Bugle entitled "Porous Metal Coated Implant and Method for Producing Same," which issued Aug. 9, 1989, describes an implant made by diffusion bonding titanium powder to a titanium or titanium Ti-6Al-4V alloy substrate. The coating provides the implant with enhanced biocompatibility. Additional examples of coated alloy implants now follow.

U.S. Pat. No. 5,725,573 entitled "Medical Implants Made of Metal Alloys Bearing Cohesive Diamond Like Carbon Coatings," which issued Mar. 10, 1998, describes a titanium alloy implant with a diamond like coating.

U.S. Pat. No. 0,703,092 by D. D. Lee et al. entitled "Hydroxyapatite Coatings and a Method of their Manufacture," which issued Jun. 9, 1998, describes orthopedic and dental implants with a crystalline calcium phosphate coating. The coating anchors the implant to the existing bone and provides the implant with enhanced biocompatibility, which increases the useful life of the implant by minimizing the likelihood of implant rejection by the body.

U. S. Patent 5,817,326 by M. A. Nastasi entitled "Processing of Hydroxyapatite Coatings on Titanium Alloy Bone Prostheses," which issued Oct. 6, 1998, describes a method of bonding hydroxyapatite to titanium alloy substrates. A titanium alloy prosthesis is coated with a sol-gel of hydroxyapatite. After the coating hardens, the resulting coated prosthesis is subjected to ion implantation to increase the adhesion of the coating and the strength of the prostheses.

Although the Ti-6Al-4V alloy is generally considered to be chemically inert, biocompatible with human tissue, and corrosion resistant to human body fluids and other corrosive environments, vanadium and aluminum are potentially toxic. Normal wear leads to implant degradation and the release of alloy elements into the body. For example, vanadium has been observed in body tissues near Ti-6V-4Al alloy implants.

Potentially biocompatible titanium alloy substitutes for Ti-6Al-4V have been described in a recent paper by K. Wang entitled "The Use and Properties of Titanium and Titanium Alloys for Medical Applications in The USA," Mater. Sci. Eng., A213 (1996) 134–137. Screw implants of the titanium alloy Ti-15Mo-5Zr-3Al (TAMZ) are described in a paper by A. Ungersbock, S. M. Perren, and O. Pohler entitled "Comparison of tissue reaction to implants of a beta titanium alloy and pure titanium. Experimental study on rabbits," J. Mater. Sci.: Materials in Medicine, 5 (1994) 788–792. Although these implants do not contain vanadium and showed promise after testing in rabbits over a three-month period, they still contain aluminum. U.S. Pat. No. 5,782,910 by J. A. Davidson entitled "Cardiovascular Implants of Enhanced Biocompatibility," which issued Jul. 21, 1998 describes medical implants made from low-modulus Ti—Nb—Zr alloys. The implants can be surface hardened with a hard, wear-resistant, hemocompatible ceramic material.

A more benign replacement for titanium alloy implants may solve the problem of the release of toxic elements into the body from degraded alloy implants. An implant of pure titanium could be the ideal replacement since it is lightweight, chemically and biologically more compatible with human tissue, and can rigidly fixate to bone better than a titanium alloy implant. Unfortunately, pure titanium lacks sufficient strength for general use as an implant material; while Ti-6Al-4V alloy has a yield strength of about 795 MPa and an ultimate strength of 860 MPa, the yield strength and ultimate strength for pure titanium are only about 380 MPa and 460 MPa, respectively.

Clearly, strong, lightweight, corrosion resistant implants that are chemically and biologically compatible with human fluids and tissue are highly desirable. Therefore, an object of the present invention is a strong, lightweight, corrosion resistant material that is chemically and biologically compatible with human fluids and tissue.

Another object of the invention is a strong, lightweight, corrosion resistant medical implant that is chemically and biologically compatible with human fluids and tissue.

Yet another object of the present invention is a method of providing ultrafine-grained titanium of sufficiently high strength for general use in medical implants and other devices.

Still another object of the present invention is a titanium implant having strength equal to or exceeding that of Ti-6Al-4V.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the present invention includes medical implants made from ultrafine-grained titanium. A coarse-grained titanium billet is placed into a lubricated first channel of a preheated equal channel angular extrusion die. The die has a second channel equal in diameter or slightly narrower than the first channel. The warmed billet is extruded through the second channel of the die, rotated about its longitudinal axis, and extruded again. After repeatedly rotating and extruding the billet, it is subjected to cold rolling and/or cold extrusion to provide ultrafine-grained titanium that is used to make medical implants.

BRIEF DESCRIPTION OF THE DRAWINGS

The accompanying drawings, which are incorporated in and form a part of the specification, illustrate embodiments of the present invention and, together with the description, serve to explain the principles of the invention.

In the FIGS.:

FIG. 1 is a schematic cross-sectional representation of a billet;

FIG. 2 is a cross-sectional schematic representation of an ECAE apparatus for extruding a billet; and FIG. 3 is a cross-sectional schematic representation of a cold extrusion apparatus that is used to extrude a billet after it has been subjected to ECAE.

DETAILED DESCRIPTION OF THE INVENTION

Briefly, the invention provides ultrafine-grained titanium of sufficient strength for making medical implants. The grain size and structure of a coarse-grained titanium billet is refined to an ultrafine-grain size by subjecting the coarse-grained billet to repeated extrusion through a warm Equal Channel Angular Extrusion (ECAE) die followed by cold rolling and/or cold extrusion, with optional subsequent annealing. The resulting ultrafine-grained titanium has strength exceeding the strength of Ti-6Al-4V and can be used to make medical implants. Unlike the titanium alloy, it does not include toxic alloy elements.

The theory of ECAE is described in a paper by V. M. Segal, V. I. Reznikov, A. E. Drobyshevskiy, and V. I. Dopylov entitled "Plastic Working of Metals by Simple Shear," which was published in Russian Metallurgy, vol. 1, pp. 99–105, (1981). Other papers and patents to Segal, Dunlop, Semaitin, and others describe the use of ECAE to process metals, alloys, plastics, and other materials into rods and plates. Segal, the pioneer of the ECAE method, has described procedures involving multiple ECAE of a billet with billet rotation between subsequent extrusions, which may be followed by forging or cold rolling.

Reference will now be made in detail to the present preferred embodiments of the invention. The accompanying drawings include schematic representations of a billet, an ECAE apparatus used to plastically deform a billet, and cold extrusion apparatus used in combination with the ECAE apparatus to provide the ultrafine-grained titanium of the present invention. Similar or identical structure is identified using identical callouts.

FIG. 1 shows a cross-sectional schematic view of a titanium billet 10 having a horizontal axis 12. FIG. 2 shows a cross-sectional schematic view of an ECAE apparatus 14 for extruding billet 10. Apparatus 14 includes die 16 and ram 18 that are made from steel or another hard, tough material. Billet 10 enters first channel 20 of die 16 through inlet 22. After heating coils 24 heat die 16 and billet 10, ram 18 applies force against billet 10 and extrudes it through second channel 26 and out of the die through exit 28. As billet 10 is extruded, it experiences shearing forces along direction 30 and undergoes severe plastic deformation. To facilitate replacement of an extruded billet into the first channel for subsequent additional extrusions, second channel 26 was slightly narrower than first channel 20. Since the dimensions of a billet are largely unaffected after extrusion, the same die can be used for multiple extrusions of a single billet. To reduce frictional forces during extrusion, a lubricant is applied to the surface of the billet, or along the channels inside the die.

According to the present invention, the ECAE extruded billet is subsequently subjected to cold processing steps that include cold rolling and/or cold extrusion. Cold rolling is preferable to cold extrusion since rolling does not require a lubricant while extrusion does. Also, multiple cold rolling steps can be performed with the same apparatus, while multiple cold extrusions require several dies since a pass through a die reduces the cross-sectional area of the billet.

FIG. 3 shows a schematic cross-sectional representation of cold extrusion apparatus 32, including a die 34 and ram 35. Die 34 includes a die channel 36 having a wide portion 38 for receiving the billet and a narrow portion 40 through which the billet is extruded and plastically deformed. The strain of the extruded billet is related to the relative reduction in cross-sectional area of the billet. For example, a billet having cross-sectional area of 400 mm$^2$ that is extruded to a cross-sectional area of 200 mm$^2$ has a strain of 50%.

Commercially pure (CP) titanium having the chemical composition shown in Table 1 was used to provide medical implants of the present invention.

TABLE 1

| Oxygen | hydrogen | Nitrogen | Carbon | Iron | Titanium |
|--------|----------|----------|--------|-------|----------|
| 0.12%  | 0.010%   | 0.04%    | 0.07%  | 0.18% | The rest |

The following example illustrates a procedure for providing the ultrafine-grained titanium for making the medical implants of the present invention. The data is summarized in entry 4 of Table 2 below. A cylindrical titanium billet 26 mm in diameter, 120 mm long, and having the composition of Table 1 with a mean grain size of 10 microns was coated with an oil based-graphite lubricant and placed inside an ECAE die having channels intersecting at an angle of 90 degrees. The die and billet were preheated to about 450° C. The billet was extruded, removed from the die, rotated clockwise 90 degrees about its longitudinal axis, placed back into the die, and extruded again. This procedure was repeated for a total of 8 extrusions. The temperature decreased to about 400° C. for the eighth extrusion. The resulting titanium billet had an equiaxed microstructure with a mean grain size of about 0.26 microns, an ultimate strength of 710 MPa, a yield strength of 640 MPa, and a ductility (i.e. an elongation to failure) of 14%. These numbers indicate greatly improved mechanical properties when compared to the unprocessed, coarse-grained titanium, which has an ultimate strength of 460 MPa and a yield strength of 380 MPa. This ultrafine-grained titanium billet was then machined to a diameter of 16 mm and subjected to multiple pass cold rolling at room temperature at a rolling speed of 0.1 meter/second. Each rolling pass decreased the dimension in the normal direction by 0.5–1 mm. Self-heating during the rolling process heated the billet to about 100° C. The rolled billet was placed into cold water between rolling passes to cool the billet to about room temperature. The total rolling strain, i.e. the reduction in cross-sectional area due to rolling, of the rolled billet after multiple passes reached about 55%. This billet had an ultimate strength of 1050 MPa, where ultimate strength is defined as the maximum tensile load that the billet can resist divided by the original cross-sectional area. The rolled billet had a yield strength of 1020 MPa, defined as the amount of stress that causes 0.2% of plastic strain. The rolled billet had a ductility of about 6%, a reduction in area at its fracture section of about 30%, and an Hv (Vickers) microhardness of about 2800 MPa. Table 2 summarizes the yield and ultimate strengths, the percent elongation, and the percent reduction in area measured along the longitudinal direction for six additional CP titanium rod-shaped billets.

TABLE 2

| Entry | Processing conditions | Ultimate Strength (MPa) | Yield Strength (MPa) | % Elongation | % Reduction in Area |
|---|---|---|---|---|---|
| 1 | Coarse grained (grain size = 10 μm) | 460 | 380 | 27% | 69% |
| 2 | ECAE, 8 passes, 450° C. to 400° C., 90 degree rotation between passes | 710 | 640 | 14% | 61% |
| 3 | ECAE (#2) + cold rolling ($\epsilon$ = 35%) | 1040 | 940 | 6.8% | 45% |
| 4 | ECAE (#2) + cold rolling ($\epsilon$ = 55%) | 1050 | 1020 | 6% | 30% |
| 5 | ECAE (#2) + cold rolling ($\epsilon$ = 75%) | 1100 | 1000 | 8% | 42% |
| 6 | ECAE (#2) + cold rolling ($\epsilon$ = 73%) + final annealing at 300° C. for 1 hour | 1037 | 942 | 12.5% | 43.5% |
| 7 | ECAE (#2) + cold rolling until $\epsilon$ = 55% + annealing at 350° C. for 1 hour after + cold rolling until $\epsilon$ = 73% + final annealing at 300° C. for 1 hour | 1049 | 954 | 12% | 40% |
| 8 | ECAE (#2) + cold extrusion ($\epsilon$ = 47%) | 930 | 910 | — | 55% |
| 9 | ECAE (#2) + cold extrusion ($\epsilon$ = 75%) | 1050 | 950 | 8 | 42% |

Billet processing conditions are summarized in the second column. A coarse-grained CP titanium billet having the composition of Table 1 was used as the starting material for each entry. Each billet was subjected to the ECAE procedure of entry #2, which included 8 extrusions through the die With a 90degree clockwise rotation around the billet longitudinal axis between subsequent extrusions. For each entry, the ECAE die was preheated to about 450° C. to heat the titanium billet. By the eighth extrusion, the die temperature decreased to about 400° C. Generally, to avoid die damage, microcracks in the billet, and recrystallization of the ultrafine grained titanium back to a coarse grain, the die temperature should be kept between about 250–500° C. Billet preheating is preferably to a temperature of about 425–475° C.

Entry 1 of Table 2 provides data for the starting coarse-grained CP titanium billet and is included for comparison. Entry 2 shows data for 8 passes through the die at a starting temperature of 450° C. and final temperature of 400° C., with 90 rotations between subsequent passes. ECAE refined the coarse grain size of the billet to a mean grain size of about 0.25–0.30 microns, and improved both the yield strength and ultimate strength from 380 MPa to 640 MPa, and from 460 MPa to 710 MPa, respectively. However, the ECAE procedure alone did not provide ultrafine-grained titanium with the strength of alloy Ti-6Al-4V, which has an ultimate strength of 860 MPa and a yield strength of about 795 MPa.

Entries 3–7 show data for ECAE combined with cold processing and provide the ultrafine-grained titanium of the present invention. Entries 3–5 show data for billets first subjected to the ECAE procedure and then subjected to cold rolling. Entries 3, 4, and 5 were subjected to cold rolling to increase the strain ($\epsilon$) to 35%, 55%, and 75% respectively. It appears that the strength of the billet increases as the strain provided by cold rolling also increases.

Entry 6 shows data for a billet subjected first to ECAE, then to cold rolling, and then to annealing at 300° C. for 1 hour. The annealing step provided the billet with a lesser ultimate strength and a lesser yield strength than that of entry 5.

Entry 7 shows data for a billet subjected first to the ECAE procedure and then to cold rolling with an intermediate annealing. The ECAE extruded billet was first cold rolled to a strain of 55%, then annealed at 350° C. for 1 hour, then cold rolled to a strain of 73%, and finally annealed at 300° C. for 1 hour. The intermediate annealing between cold rolling to a strain of 73% appears to provide the billet with slightly higher ultimate and yield strength than that for entry 6.

Entries 8 and 9 show data for titanium billets subjected first to the ECAE procedure of entry 2, and then to room temperature cold extrusion to final strains of 47% and 75%, respectively. The final ultimate and yield strength for both titanium billets exceeds that for alloy Ti-6Al-4V.

The effect of the annealing on the grain size of ECAE extruded billets was examined. The grain sizes of a billet first subjected to the 8-extrusion ECAE procedure and then annealed at 300° C. for 0.5 hr were not visibly affected. An ECAE extruded billet that was annealed at 500° C. for 0.5 hr was completely recrystallized, the resulting coarse grained billet having grain sizes of about 2–4 μm.

The ultimate strength, yield strength, and hardness of the coarse-grained titanium billet were improved after a single extrusion through the preheated die. Two to four extrusions provided the billet with a grain size of about 2–3 μm and a non-uniform microstructure. Mechanical properties were optimized after 8 extrusions through a preheated die with a 90-degree billet rotation between extrusions. In particular, the invention provides ultrafine-grained titanium having an ultimate strength of about 860–1100 MPa and a yield strength of about 795–1050 MPa.

Medical implants of the present invention were machined from the ultrafine-grained titanium. These included plates, threaded and non-threaded rods, and screw implants. They were used to reinforce a variety of damaged bones. Dental implants were also prepared and were used to replace missing teeth.

Other devices such as tubes, wires, nails and foil, can also be fabricated. For example, hollow implants can be machined using standard machining techniques. Since they are lighter and less stiff than solid implants, they would provide reduced stress shielding to attached bone that could decrease the likelihood of implant loosening and increase the useful life of the implant.

Implants fabricated for conditions of both cyclic loading and interaction with living tissues may include additional features. Medical implants of the present invention include coated implants. A coating of titanium oxide, hydroxyapatite, or other biocompatible material imparts additional bioinert and bioactive properties to the implant by improving the wear resistance and adhesion of the implant to the attached bone.

In conclusion, utrafine-grained titanium of the present invention is as strong or stronger than titanium alloy Ti6Al- 4V that is commonly used to make medical implants. In particular, the invention provides ultrafine-grained titanium having an ultimate strength of about 860–1100 MPa and a yield strength of about 795–1050 MPa. The combination of biocompatibility, high strength, and lack of toxic alloying elements makes implants of the present invention an attractive alternative to implants made from Ti-6Al-4V and other materials that are currently used.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A medical implant comprising ultrafine-grained titanium made by the process comprising the steps of:
   (a) placing a coarse-grained titanium billet into a lubricated first channel of a preheated equal channel angular extrusion die and extruding the billet through a second channel of the die that intersects with the first channel;
   (b) rotating the extruded billet a chosen amount around its longitudinal axis and extruding the rotated billet again;
   (c) repeating step (b) a chosen number of times;
   (d) subjecting the product of step (c) to cold processing; and
   (e) fabricating the medical implant from the product of step (d).

2. The medical implant of claim 1, the cold processing of step (d) comprising cold rolling.

3. The medical implant of claim 1, the cold processing of step (d) comprising cold extrusion.

4. The medical implant of claim 1, the process further comprising the step of annealing the billet of step (c) after extruding it a chosen number of times.

5. The medical implant of claim 1, the process further comprising the step of annealing the cold processed billet of step (d).

6. The medical implant of claim 1, wherein the lubricant comprises an oil-based graphite lubricant.

7. The medical implant of claim 1, wherein step (b) includes rotating the extruded billet about 90 degrees around its longitudinal axis before extruding it again.

8. The medical implant of claim 1, wherein step (b) is repeated for a total of eight extrusions.

9. The medical implant of claim 1, wherein the die is preheated to a temperature of about 250–500° C. prior to extrusion.

10. The medical implant of claim 1, wherein the die is preheated to a temperature of about 425–475° C. to warm the billet before extrusion.

11. The medical implant of claim 1, wherein the die is preheated to a temperature of about 450° C. to warm the billet prior to extrusion.

12. The medical implant of claim 1, wherein the ultrafine-grained titanium has an ultimate strength of about 860–1100 MPa.

13. The medical implant of claim 1, wherein the ultrafine-grained titanium has a yield strength of about 795–1050 MPa.

14. The medical implant of claim 1, said implant being selected from the group consisting of wires, rods, plates, screws, nails, and tubes.

15. The medical implant of claim 1, said implant comprising a biocompatible coating.

16. The medical implant of claim 15, wherein the coating comprises titanium dioxide.

17. The medical implant of claim 15, wherein the coating comprises hydroxyapatite.

18. A medical implant, comprising ultrafine-grained titanium having an ultimate strength of about 860–1100 MPa and yield strength of about 795–1050 MPa.

19. The implant of claim 18, wherein said implant is selected from the group consisting of wire, rods, plates, screws, nails, and tubes.

20. The medical implant of claim 18, further comprising a biocompatible coating.

21. The medical implant of claim 20, wherein said coating comprises titanium dioxide.

22. The medical implant of claim 20, wherein said coating comprises hydroxyapatite.

23. The medical implant of claim 18, wherein said implant comprises a dental implant.

24. A method of producing ultrafine-grained titanium, comprising the steps of:
   (a) placing a coarse-grained titanium billet into a lubricated first channel of a preheated equal channel angular extrusion die and extruding it through a second channel of the die that intersects with the first channel;
   (b) rotating the extruded billet a chosen amount around its longitudinal axis and extruding the billet again;
   (c) repeating step (b) a chosen number of times; and
   (d) subjecting the product billet of step (c) to cold processing to produce said ultrafine-grained titanium.

25. The method of claim 24, wherein the cold processing of step (d) comprises cold rolling.

26. The method of claim 24, wherein the cold processing of step (d) comprises cold extrusion.

27. The method of claim 24, further comprising the step of annealing the billet after extruding it for a chosen number of times.

28. The method of claim 24, further comprising the step of annealing the cold processed billet of step (d).

29. The method of claim 24, wherein the lubricated first channel comprises an oil-based graphite lubricant.

30. The method of claim 24, wherein step (b) includes rotating, the extruded billet about 90 degrees around its longitudinal axis before extruding it again.

31. The method of claim 24, wherein step (c) comprises repeating step (b) for a total of eight passes.

32. The method of claim 24, wherein the die is preheated to a temperature of about 250–500° C.

33. The method of claim 24, wherein the die is preheated to a temperature of about 425–475° C.

34. The method of claim 24, wherein the die is preheated to a temperature of about 450° C.

35. The method of claim 24, further comprising the step of fabricating a device from the ultrafine-grained titanium, the device selected from the group consisting of wires, rods, plates, tubes, foil, screws, and nails.

36. Ultrafine-grained titanium having an ultimate strength of about 860–1100 MPa and yield strength of about 795–1050 MPa.

37. A device comprising ultrafine-grained titanium made by the process comprising the steps of:
   (a) placing a coarse-grained titanium billet into a lubricated first channel of a preheated equal channel angular extrusion die and extruding the billet through a second channel of the die that intersects with the first channel;
   (b) rotating the extruded billet a chosen amount around its longitudinal axis and extruding the rotated billet again;

(c) repeating step (b) a chosen number of times;

(d) subjecting the product of step (c) to cold processing; and (e) fabricating the device from the product of step (d).

38. The device of claim 37, the cold processing of step (d) comprising cold rolling.

39. The device of claim 37, the cold processing of step (d) comprising cold extrusion.

40. The device of claim 37, the process further comprising the step of annealing the billet of step (c) after extruding it a chosen number of times.

41. The device of claim 37, the process further comprising the step of annealing the cold processed billet of step (d).

42. The device of claim 37, wherein the lubricant comprises an oil-based graphite lubricant.

43. The device of claim 37, wherein step (b) includes rotating the extruded billet about 90 degrees around its longitudinal axis before extruding it again.

44. The device of claim 37, wherein step (b) is repeated for a total of eight extrusions.

45. The device of claim 37, wherein the die is preheated to a temperature of about 250–500° C. prior to extrusion.

46. The device of claim 37, wherein the die is preheated to a temperature of about 425–475° C. to warm the billet before extrusion.

47. The device of claim 37, wherein the die is preheated to a temperature of about 450° C. to warm the billet prior to extrusion.

48. The device of claim 37, wherein the ultrafine-grained titanium has an ultimate strength of about 860–1110 MPa.

49. The device of claim 37, wherein the ultrafine-grained titanium has a yield strength of about 795–1050 MPa.

50. A device comprising ultrafine-grained titanium, the titanium having an ultimate strength of about 860–1100 MPa and a yield strength of about 795–1050 MPa.

* * * * *